United States Patent
Miyake et al.

(10) Patent No.: US 10,882,805 B2
(45) Date of Patent: Jan. 5, 2021

(54) PROCESSES FOR PREPARING 4-METHYL-5-NONANONE AND 4-METHYL-5-NONANOL

(71) Applicant: Shin-Etsu Chemical Co., Ltd., Tokyo (JP)

(72) Inventors: Yuki Miyake, Niigata (JP); Takeshi Kinsho, Niigata (JP); Yusuke Nagae, Niigata (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 16/722,123

(22) Filed: Dec. 20, 2019

(65) Prior Publication Data

US 2020/0199052 A1    Jun. 25, 2020

(30) Foreign Application Priority Data

Dec. 21, 2018    (JP) ................ 2018-239591

(51) Int. Cl.
| | | |
|---|---|---|
| C07C 29/143 | (2006.01) | |
| C07C 51/487 | (2006.01) | |
| C07C 51/56 | (2006.01) | |
| C07C 45/45 | (2006.01) | |

(52) U.S. Cl.
CPC .......... *C07C 29/143* (2013.01); *C07C 45/455* (2013.01); *C07C 51/487* (2013.01); *C07C 51/56* (2013.01)

(58) Field of Classification Search
CPC ..... C07C 29/143; C07C 51/487; C07C 51/56; C07C 45/455
See application file for complete search history.

(56) References Cited

U.S. PATENT DOCUMENTS

| | | | |
|---|---|---|---|
| 6,864,394 B2 | 3/2005 | Goossen et al. | |
| 7,175,764 B2 | 2/2007 | Weiss et al. | |
| 10,392,325 B2 | 8/2019 | Kurihara et al. | |

FOREIGN PATENT DOCUMENTS

| | | | |
|---|---|---|---|
| CN | 1117052 | | 8/2003 |
| IN | 201504905 I4 | * | 3/2017 |
| JP | 2526963 | | 8/1996 |

OTHER PUBLICATIONS

Dang et al. ("A facile synthesis of racemic aggregation pheromones of palm pests, Rhinoceros beetle and Rhynchophorus weevil", Arkivoc, Oct. 2017, part v, pp. 187-195).*
U.S. Appl. No. 16/722,138, Miyake et al., filed Dec. 20, 2019.

Maruoka et al. "Methylaluminum Bis(4-bromo-2,6-di-tert-butylphenoxide) as a Key Reagent for Effecting Primary alpha-Alkylation of Carbonyl Compounds" Journal of the American Chemical Society, 114:4422-4423 (1992).
Oehlschlager et al. "Structure, Chirality, and Field Testing of a Male-Produced Aggregation Pheromone of Asian Palm Weevil *Rhynchophorus bilineatus* (Montr.) (Coleoptera: Curculionidae)" Journal of Chemical Ecology, 21(10):1619-1629 (1995).
Perez et al. "Pheromone Chirality of Asian Palm Weevils, *Rhynchophorus ferrugineus* (OLIV.) and *R. vulneratus* (PANZ.) (Coleoptera: Curculionidae)" Journal of Chemical Ecology, 22(2):357-368 (1996).
Dang et al. "A facile synthesis of racemic aggregation pheromones of palm pests, Rhinoceros beetle and Rhynchophorous weevil" ARKIVOC, 2017(5):187-195 (2017).
Extended European Search Report corresponding to European Patent Application No. 19217009.0 (6 pages) (dated May 7, 2020).

(Continued)

*Primary Examiner* — Rosalynd A Keys
(74) *Attorney, Agent, or Firm* — Myers Bigel, P.A.

(57) ABSTRACT

The present invention provides a process for preparing 4-methyl-5-nonanone of the following formula (3): the process comprising at least a step of subjecting 2-methyl-pentanoic anhydride of the following formula (1) and an n-butyl nucleophilic reagent of the following general formula (2) in which M represents Li, $MgZ^1$, or $ZnZ^1$, wherein $Z^1$ represents a halogen atom or an n-butyl group, to a nucleophilic substitution. reaction Coproduce 4-methyl-5-nonanone (3), as well as a process for preparing 4-methyl-5-nonanol of the following formula (5), the process comprising at least steps of preparing 4-methyl-5-nonanone; and subjecting the obtained 4-methyl-5-nonanone and a reducing agent to a reduction reaction to produce 4-methyl-5-nonanol (5).

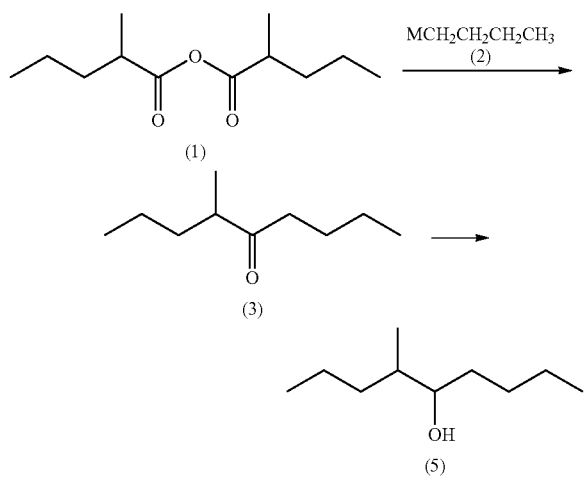

11 Claims, No Drawings

(56) References Cited

OTHER PUBLICATIONS

Onaka et al. "A Convenient Method for the Direct Preparation of Ketones from 2-(6-(2-Methoxyethyl)Pyridyl) Carboxylates and Alkyl Iodides by Use of Zinc Dust and a Catalytic Amount of Nickel Dichloride" Chemistry Letters, pp. 531-534 (1981).
Ahn et al. "Cerium(III) Chloride Remarkably Increases the Rates of Formation and Yields of Ketones in The Reaction of Lithium Carboxylates with Organolithiums" Tetrahedron Letters, 35(2):203-206 (1994).
Jorgenson, Margaret J. "Preparation of Ketones from the Reaction of Organolithium Reagents with Carboxylic Acids" Organic Reactions, Chapter 1, pp. 1-97 (1970).
Rubottom et al. "Preparation of Methyl Ketones by the Sequential Treatment of Carboxylic Acids with Methyllithium and Chlorotrimethylsilane" Journal of Organic Chemistry, 48:1550-1552 (1983).

\* cited by examiner

PROCESSES FOR PREPARING 4-METHYL-5-NONANONE AND 4-METHYL-5-NONANOL

CROSS-REFERENCE TO RELATED APPLICATION

This U.S. nonprovisional application claims priority to Japanese Application No. 2018-239591 filed Dec. 21, 2018, the entire contents of which are incorporated herein by reference.

TECHNICAL FIELD

The present invention relates to processes for preparing 4-methyl-5-nonanone and 4-methyl-5-nonanol which are known as an aggregation pheromone of red palm weevil (scientific name; *Rhynchophorus ferrugineus* e.g. *Rhynchophorus ferrugineus Olivier*) which is pest of palm trees.

BACKGROUND ART

The red palm weevil is a key pest of plants of the family Palmae such as date palm, coconut, oil palm, and betel palm. Adults of the red palm weevil enter the trunk of a palm tree and lay eggs therein. Meanwhile, their larvae eat the inside of the tree, whereby weakening and eventually killing the plant. The red palm weevil is a species native in South Asia and Melanesia. It has spread to Southeast Asia, Middle East, North Africa, Europe, the United States of America, and others and is now causing a serious damage to palmae plants over wide areas. Adults and larvae of the red palm weevil move into a palm tree, so that they cannot easily be controlled by an insecticide. Mass trapping with an aggregation pheromone has been applied throughout the world to control the insect.

It has been revealed that the aggregation pheromone of the red palm weevil is a 10:1 to 9:1 (weight ratio) mixture of 4-methyl-5-nonanonl and 4-methyl-5-nonanol (Non-Patent Literature 1, mentioned below). Processes for synthesizing these compounds were reported. 4-Methyl-5-nonanonl is synthesized by activating 5-nonanonl with methylaluminum bis(4-bromo-2,6-di-tert-butylphenoxide) at −40° C. in a solvent dichloromethane, which is then reacted with methyl triflate (Non-Patent Literature 2, mentioned below). 4-Methyl-5-nonanol is synthesized by reacting 2-methyl-1-pentanal with n-butyllithium (Non-Patent Literature 3, mentioned below).

LIST OF THE PRIOR ART

[Non-Patent Literature 1] A. C. Oehlschlager et al., J. Chem. Ecol., 1996, 22(2), 357-368.

[Non-Patent Literature 2] H. Yamamoto et al., J. Am, Chem, Soc., 1992, 114, 4422-4423.

[Non-Patent Literature 3] A. C. Oehlschlager et al., J. Chem. Ecol., 1995, 21(10), 1619-1629.

SUMMARY OF THE INVENTION

However, in Non-Patent Literature 2, carcinogenic methyl triflate is used as methylating agent and, further, a special aluminum. reagent not easily available as a general reagent is used in an equivalent amount or more. Moreover, in Non-Patent Literature 2, a reactor equipped with a special cooling device is required for carrying out the reaction at −40° C., but such a reactor is difficult to industrially manufacture. In Non-Patent Literature 3, the expensive lithium reagent is used and, further, a yield is as low as 67%. This is presumable because an alcohol formed in the nucleophilic addition reaction between 2-methyl-1-pentanal and n-butyllithium changes to a corresponding ketone by hydride transfer, and the ketone reacts with n-butyllithium again to form a tertiary alcohol as a by-product.

The present invention has been made in these circumstances, and aims to provide efficient and economical processes for preparing 4-methyl-5nonanone and 4-methyl-5-nonanol.

As a result of the intensive researches to overcome the aforesaid problems of the prior art, the present inventors have found that 4-methyl-1-nonanone is prepared in a high yield and a high purity by a nucleophilic substitution reaction between 2-methylpentanoic anhydride which is synthesized in a large amount at low costs and an n-butyl nucleophilic reagent which is industrially available and is conveniently prepared, and thus have completed the present invention. The present inventors have also found that 4-methyl-5-nonanol is prepared in a high yield and a high purity by subjecting 4-methyl-5-nonanone to a reduction reaction, and thus have completed the present invention.

In one aspect of the present invention, there is provided a process for preparing 4-methyl-5-nonanone of the following formula (3):

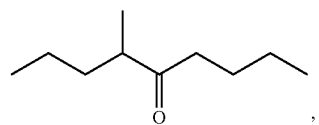

(3)

the process comprising at least a step of subjecting 2-methylpentanoic anhydride of the following formula (1):

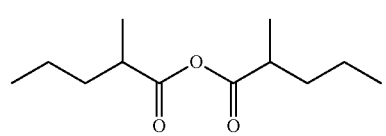

(1)

and an n-butyl nucleophilic reagent of the following general formula (2):

MCH$_2$CH$_2$CH$_2$CH$_3$   (2)

in which M represents Li, MgZ$^1$, or ZnZ$^1$, wherein Z$^1$ represents a halogen atom or an n-butyl group,
to a nucleophilic substitution reaction to produce 4-methyl-5-nonanone (3).

In another aspect of the present invention, there is also provided a process for preparing 4-methyl-5-nonanol of the following formula (5):

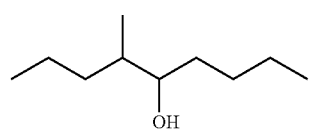

(5)

the process comprising at least steps of
preparing 4-methyl-5-nonanone (3) according to the aforesaid process, and
subjecting the obtained 4-methyl-5-nonanone and a reducing agent to a reduction reaction to produce 4-methyl-5-nonanol (5).

The present invention makes it possible to prepare 4-methyl-5-nonanone and 4-methyl-5-nonanol both in a high purity, a high yield, at low costs and in shorter steps.

DETAILED DESCRIPTION OF THE INVENTION

A. Process for Preparing 4-methyl-5-nonanone (3)

First, a process for preparing 2-methylpentanoic anhydride of the following general formula (1) to be used as a raw material to be used in a process for preparing 4-methyl-5-nonanone (3) will be described hereinafter. 2-Methylpentanoic anhydride (1) is obtained in a known synthesis process. 2-Methylpentanoic anhydride (1) is obtained, for example, by a condensation reaction of a 2-methylpentanoic acid of the following formula (4), as shown in the following chemical reaction formula.

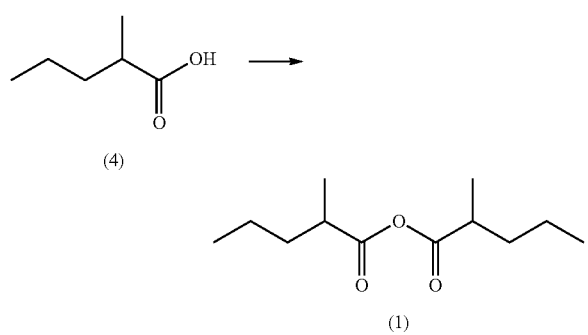

Examples of the 2-methylpentanoic acid (4) include (R)-2-methylpentanoic acid of the following formula (4-1), (S)-2-methylpentanoic acid of the following formula (4-2), and a racemate and scalemic mixtures thereof.

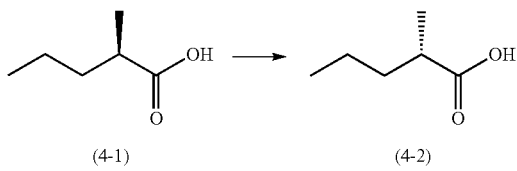

The 2-methylpentanoic acid (4) may be commercially available one or any be synthesized in house.

The condensation reaction may proceed under heating. A condensing agent is preferably used in view of the reaction efficiency.

Examples of the condensing agent include acid anhydrides of a carboxylic acid compound having from 1 to 5 carbon atoms such as formic anhydride, acetic anhydride, propionic anhydride, butanoic anhydride, 2-methylbutanoic anhydride, 3-methylbutanoic anhydride, and pentanoic anhydride; carboxylic acid compounds such as formic acid, acetic acid, trifluoroacetic acid, dichloroacetic acid, oxalic acid, tartaric acid, and citric acid; sulfonic acid compounds such as p-toluenesulfonic acid, benzenesulfonic acid, and methanesulfonic acid; inorganic acids such as hydrochloric acid, hydrobromic acid, hydroiodic acid, sulfuric acid, nitric acid, phosphoric acid, and boric acid; and carbodiimide compounds such as N,N'-dicyclohexylcarbodiimide (DCC), 1-(3-dimethylaminopropyl)-3-ethylcarbodiimide (EDC), and N,N'-diisopropylcarbodiimide (DIC). Formic acid, acetic acid, and acetic anhydride are preferred, with acetic anhydride being more preferred, in view of the handling.

The condensing agent may be used either alone or in combination thereof. The condensing agent may be commercially available one.

An amount of the condensing agent is preferably from 1.0 to 4.0 mol, more preferably front 1.3 to 2.7 mol, per mol of the 2-methylpentanoic acid (4) in view of the reactivity.

In the condensation reaction, a solvent may be used, if necessary. Examples of the solvent include hydrocarbon solvents such as toluene, xylene, and hexane; ether solvents such as tetrahydrofuran and diethyl ether; and polar solvents such as N,N-dimethylformamide, N,N-dimethylacetamide, N-methylpyrrolidone, dimethyl sulfoxide, and acetonitrile.

The solvent may be used either alone or in combination thereof. The solvent may be commercially available one.

An amount of the solvent is preferably from 0 to 2000 g per mol of the 2-methylpentanoic acid (4) in view of the reactivity.

When the condensing agent used is in a liquid form, the condensing agent may work also as a solvent. Examples of the liquid condensing agent include acid anhydrides of carboxylic acids having from 1 to 5 carbon atoms such as formic anhydride, acetic anhydride, propionic anhydride, butanoic anhydride, 2-methylbutanoic anhydride, 3-methylbutanoic anhydride, and pentanoic anhydride; and carboxylic acids such as formic acid, acetic acid, trifluoroacetic acid, dichloroacetic acid, oxalic acid, tartaric acid, and citric acid. By using them, use of another solvent is not required or an amount thereof can be reduced.

An amount of the condensing agent which works also as a solvent is preferably more than 4.0 and 10.0 mol or less, more preferably from 4.5 to 8.5 mol, per mol of the 2-methylpentanoic acid (4) in view of the productivity.

A temperature of the condensation reaction differs, depending on a solvent used and/or a degree of evacuation and is preferably from 35 to 189° C. in view of the reactivity.

A reaction time differs, depending on a solvent used and/or a production scale and is preferably from 4 to 35 hours in view of the reactivity.

The condensation reaction may be carried out while distilling off water generated by dehydration condensation and/or a carboxylic acid generated when an acid anhydride is used as the condensing agent, an acid anhydride generated by a disproportionation reaction, and other by-products, under heating and/or reduced pressure to enhance the condensation reaction.

Conditions of the distillation duller, depending on reaction conditions and/or a condensing agent used. For example, when acetic anhydride is used as the condensing agent (including a case where acetic anhydride Works also as a solvent), the 2-methylpentanoic acid (4) is reacted with acetic anhydride at normal pressure (760 mmHg) at a temperature (internal temperature) of the reaction mixture in a reactor of from 140 to 180° C. for 0.5 to 10 hours to form acetic 2-methylpentanoic anhydride and acetic acid. Next, the formation of acetic 2-methylpentantoic anhydride is continued at 140 to 180° C. and normal pressure while distilling acetic acid off, until an acetic content becomes preferably at most 10.0%, more preferably 0.1 to 5.0%, in the distillate containing at least acetic acid, acetic anhydride, and acetic 2-methylpentanoic anhydride.

A content of acetic acid in the distillate containing at least acetic acid, acetic anhydride, and acetic 2-methylpentanoic anhydride is defined by the following equation.

Content of acetic acid in the distillate containing at least acetic acid, acetic anhydride, and acetic 2-methylpentanoic anhydride={(peak area of acetic acid)/(sum of peak areas of acetic acid, acetic anhydride, and acetic 2-methylpentanoic anhydride)}×100

The peak areas are determined by various analysis methods such as gas chromatography and liquid chromatography.

A disproportionation reaction of acetic 2-methylpentanoic anhydride is caused at a pressure gradually reduced to form 55 to 75 mmHg and an internal temperature of from 140 to 180° C. to sufficiently form 2-methylpentanoic anhydride and acetic anhydride. It is to be noted that the term "internal temperature" means a temperature of the reaction mixture in the reactor and has the same meaning as a reaction temperature.

The acetic anhydride used as a condensing agent and the acetic anhydride formed by the disproportionation reaction are distilled off until the content of acetic anhydride in the distillate containing at least acetic anhydride, 2-methylpentanol, acetic 2-methylpentanoic anhydride, and 2-methylpentanoic anhydride reaches preferably 1.0% or less, more preferably from 0.1 to 0.5%.

A content of acetic anhydride in the distillate containing at least acetic anhydride, 2-methylpentanol, acetic 2-methylpentanoic anhydride, and 2-methylpentanoic anhydride is defined by the following equation.

Content of acetic anhydride in the distillate containing at least acetic anhydride, 2-methylpentanol, acetic 2-methylpentanoic anhydride, and 2-methylpentanoic anhydride={(peak area of acetic anhydride)/(sum of peak areas of acetic anhydride, 2-methylpentanol, acetic 2-methylpentanoic anhydride, and 2-methylpentanoic anhydride)}×100

The peak areas are determined by various analysis methods such as gas chromatography and liquid chromatography.

Lastly, the pressure is reduced to from 1 to 10 mmHg and adjusting the internal temperature to front 120 to 160° C. to obtain 2-methylpentanoic anhydride (1) efficiently.

Examples of the 2-methylpentanoic anhydride (1) include (R)-2-methylpentanoic-(R)-2-methylpentanoic anhydride of the following formula (1-1), (S)-2-methylpentanoic-(S)-2-methylpentanoic anhydride of the following formula (1-2), and (R)-2-methylpentanoic-(S)-2-methylpentanoic anhydride of the following formula (1-3) which compound is a meso form and is the same compound as (S)-2-methylpentanoic-(R)-2-methylpentanoic anhydride, and a racemate, diastereomeric mixtures, and scalemic mixtures thereof.

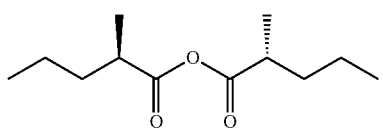
(1-1)

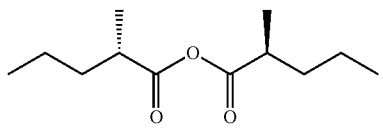
(1-2)

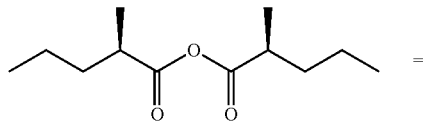
(1-3)

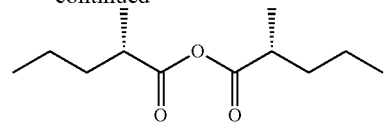

Next, a process of the following chemical reaction preparing the 4-methyl-5-nonanone (3) will be explained. This preparation process includes a nucleophilic substitution reaction between the aforesaid 2-methylpentanoic anhydride (1) and an n-butyl nucleophilic reagent of the following general formula (2), and a subsequent hydrolysis to obtain the 4-methyl-5-nonanone (3).

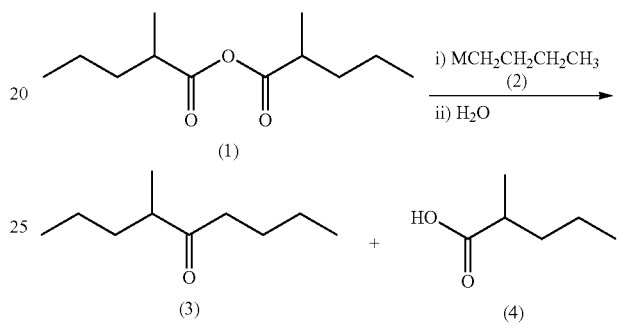

M in the n-butyl nucleophilic reagent (2) represents Li, $MgZ^1$, or $ZnZ^1$, and $Z^1$ represents a halogen atom or at n-butyl group. Examples of the halogen atom include a chlorine atom, a bromine atom, and an iodine atom.

Specific examples of the n-butyl nucleophilic reagent (2) include butylmagunesium halide reagents such as n-butyl-lithium, butylmagnesium chloride, and butylmagnesium bromide; and butyl zinc reagents such as dibutyl zinc. The butylmagunesium halide reagents are preferred in view of the versatility.

The n-butyl nucleophilic reagent (2) may be used either alone or in combination thereof. The n-butyl nucleophilic reagent (2) may be commercially available one or may be synthesized in house.

The n-butyl nucleophilic reagent (2) can be prepared in a manner known per se in the art. For instance, 1-halobutane compound of the following general formula (6) is reacted with magnesium in a solvent to produce the butylmagnesium halide reagent (2), as shown in the following chemical reaction formula.

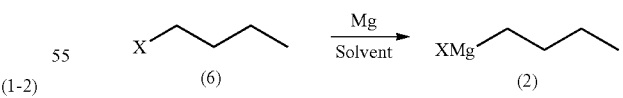

X in the 1-halobutane compound (6) represents a halogen atom. Examples of the halogen atom include a chlorine atom, a bromine atom, and an iodine atom.

Specific examples of the 1-halobutane compound (6) include 1-chlorobutane, 1-bromobutane and 1-iodobutane.

The 1-halobutane compound (6) may be used either alone or in combination thereof. The 1-halobutane compound (6) may be commercially available one or may be synthesized in house.

An amount of magnesium to be used in preparing the butylmagunesium halide reagents (2) from the 1-halobutane compound (6) is preferably from 1.0 to 2.0 gram atoms per mol of the 1-halobutane compound (6) in view of the completion of the reaction.

Examples of the solvent include ether solvents such as tetrahydrofuran, diethyl ether, and 4-methyltetrahydropyran; and hydrocarbon solvents such as toluene, xylene, and hexane. Tetrahydrofuran is preferred in view of the reaction rate in the formation of the Grignard reagent.

The solvent may be used either alone or in combination thereof. The solvent may be commercially available one.

An amount of the solvent is preferably from 100 to 1000 g per mol of the 1-halobutane compound (6) in view of the reactivity.

A reaction temperature differs, depending on a solvent used and is preferably from 30 to 120° C. in view of the reactivity.

A reaction time differs, depending on a solvent used and/or a production scale and is preferably from 1 to 30 hours in view of the reactivity.

A solvent may be used in the aforesaid nucleophilic substitution reaction, if necessary. Examples of the solvent include hydrocarbon solvents such as toluene, xylene, and hexane; ether solvents such as tetrahydrofuran, 4-methyltetrahydropyran, and diethyl ether; and polar solvents such as N,N-dimethylformamide, N,N-dimethylacetamide, N-methylpyrrolidone, dimethyl sulfoxide, and acetonitrile. Toluene, tetrahydrofuran, 4-methyltetrahydropyran, and acetonitrile are preferred, with tetrahydrofuran being more preferred, in view of the reactivity.

The solvent may be used either alone or in combination thereof. The solvent may be commercially available one.

An amount of the solvent is preferably from 30 to 2000 g per mol of the 2-methylpentanoic anhydride (1) in view of the reactivity.

A temperature of the nucleophilic substitution reaction differs, depending on the butyl nucleophilic reagent used and is preferably from −78 to 70° C., amore preferably from −20 to 25° C., in view of the reactivity.

A reaction time differs, depending on a solvent used and/or a production scale and is preferably from 3 to 45 hours in view of the reactivity.

The aforesaid hydrolysis is carried out using an acid and water.

Examples of the acid include organic acids such as formic acid, acetic acid, trifluoroacetic acid, dichloroacetic acid, oxalic acid, tartaric acid, citric acid, p-toluenesulfonic acid, benzenesulfonic acid, and methanesulfonic acid; and inorganic acids such as hydrochloric acid, hydrobromic acid, hydroiodic acid, sulfuric acid, nitric acid, phosphoric acid, and boric acid. Formic acid, acetic acid, and hydrochloric acid are preferred in view of the economy.

An amount of the acid is preferably from 1 to 5 mol per mol of the 2-methylpentanoic anhydride (1) in view of the reactivity.

An amount of water is preferably from 100 to 1000 g per mol of the 2-methylpentanoic anhydride (1) in view of the solubility.

Examples of the 4-methyl-5-nonanone (13) include (4R)-4-methyl-5-nonanone of the following formula (3-1) and (4S)-4-methyl-5-nonanone of the following formula (3-2), and a racemate and scalemic mixtures thereof.

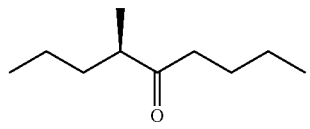

(3-1)

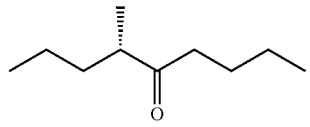

(3-2)

During or after the aforesaid nucleophilic substitution reaction, 2-methylpentanoic acid (4) which was by-produced in the nucleophilic substitution reaction may be recovered; the recovered 2-methylpentanoic acid (4) is condensation-reacted into 2-methylpentanoic anhydride (1); and the 2-methylpentanoic anhydride (1) thus obtained is used in the nucleophilic substitution reaction or is used in a subsequent nucleophilic substitution reaction as a raw material for the subsequent nucleophilic substitution reaction to repeat the subsequent nucleophilic substitution reaction.

First, the step of recovering 2-methylpentanoic acid (4) which was by-produced in the nucleophilic substitution reaction will be explained.

In the nucleophilic substitution reaction where the 4-methyl-5-nonanone (3) is produced, 2-methylpentanoic acid (4) is by-produced from the 2-methylpentanoic anhydride (1).

Examples of a method for recovering the 2-methylpentanoic acid (4) include a method of separating the 2-methylpentanoic acid (4) from the 4-methyl-5-nonanone (3) and recovering the 2-methylpentanoic acid (4) in post-treatment after the nucleophilic substitution reaction, a method of separating the 2-methylpentanoic acid (4) from the 4-methyl-5-nonanone (3) by silica gel column chromatography and recovering the 2-methylpentanoic acid (4), and a method of separating the 2-methylpentanoic acid (4) from the 4-methyl-5-nonanone (3) by distillation and recovering the 2-methylpentanoic acid (4). For example, the method of separating the 2-methylpentanoic acid (4) from the 4-methyl-5-nonanone (3) and recovering the 2-methylpentanoic acid (4) in the post-treatment after the nucleophilic substitution reaction is preferred, because the separation of the 2-methylpentanoic acid (4) from the 4-methyl-5-nonanone (3) is easy.

The aforesaid recovering method in the post-treatment is specifically shown by the following chemical reaction formula. As described above, the reaction mixture (organic phase) containing the 4-methyl-5-nonanone (3) and the 2-methylpentanoic acid (4) obtained in the nucleophilic substitution reaction is neutralized by adding water and a base thereto successively or simultaneously or neutralized in the presence of an aqueous solution of phase to obtain an organic phase containing the 4-methyl-5-nonanone (3) and an aqueous phase containing a sail of 2-methylpentanoic acid (7) (neutralization step). After separation of the aqueous phase, an acid is added thereto to liberate the 2-methylpentanoic acid (4). Thus, the 2-methylpentanoic acid (4) is obtained (liberation step).

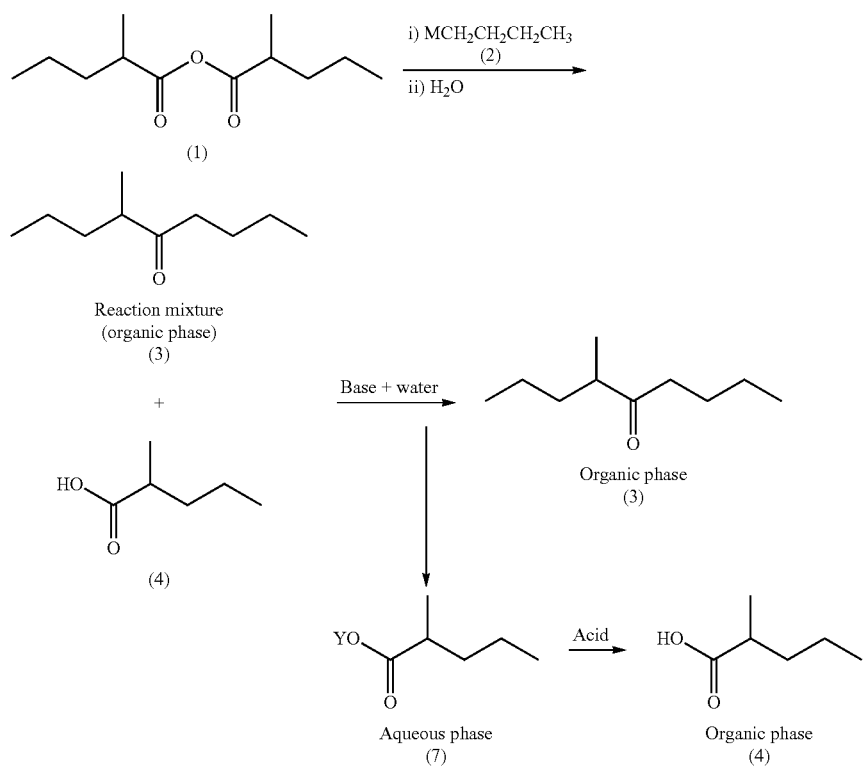

Reaction mixture (organic phase) (3)

+

(4)

Base + water →

Organic phase (3)

↓

Aqueous phase (7)

Acid →

Organic phase (4)

The 2-methylpentanoic acid (4) is neutralized with the base into the salt of 2-methylpentanoic acid (7) in the neutralization step. The salt of 2-methylpentanoic acid (7) is soluble in water. Therefore, the 4-methyl-5-nonanone (3) is easily separated from the salt of 2-methylpentanoic acid (7). By liquid separation, the organic phase containing the 4-methyl-5-nonanone (3) and the aqueous phase containing the salt of 2-methylpentanoic acid (7) is obtained.

Examples of the base include alkali metal hydroxides such as lithium hydroxide, sodium hydroxide, and potassium hydroxide; alkaline earth metal hydroxides such as calcium hydroxide, magnesium hydroxide, and barium hydroxide; alkali metal carbonates such as sodium carbonate and potassium carbonate; alkaline earth metal carbonates such as calcium carbonate, magnesium carbonate, and barium carbonate; alkali metal hydrogen carbonates such as sodium hydrogen carbonate and potassium hydrogen carbonate; and alkaline earth metal hydrogen carbonates such as calcium hydrogen carbonate and magnesium hydrogen carbonate. The alkali metal hydroxides such as sodium hydroxide are preferred in view of handling.

An amount of the base is preferably from 1.0 to 5.0 mol per mol of the 2-methylpentanoic anhydride (1) used in the aforesaid nucleophilic substitution reaction in view of a recovery yield.

The base may be used either alone or in combination thereof. The base may be commercially available one.

When the base is in a solid form, it may be used as such or may be dissolved in a solvent and/or water used in the nucleophilic substitution reaction.

An amount of water is preferably from 300 to 3000 g per mol of the 2-methylpentanoic anhydride (1) used in the aforesaid nucleophilic substitution reaction in view of the solubility of the salt of 2-methylpentanoic acid (7).

A temperature of the neutralization reaction is preferably from −20 to 70° C., more preferably from 0 to 40° C., in view of the reactivity.

A reaction time differs, depending on a production scale and/or heat removal ability and is preferably from 0.1 to 20 hours in view of the reactivity.

A pH of the aqueous phase in the neutralization step is preferably 10.0 or higher, more preferably from 12.0 to 14.0, in view of the recovery yield of the 2-methylpentanoic acid (4). The pH may be determined by, for example test strip or a pH meter after adjusting a temperature of the liquid object at 25° C.

The salt of 2-methylpentanoic acid is represented by the following formula (7) wherein Y represents Li, Na, K, $CaZ^2$, $MgZ^2$, or $BaZ^2$, and $Z^2$ represents a carboxylate ion of 2-methylpentanoic acid, OH, or $HCO_3$.

(7)

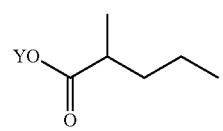

Preferred examples of the salt of 2-methylpentanoic acid (7) depend on a base used, and generally include alkali metal salts of 2-methylpentanoic acid such as sodium 2-methylpentanoate and potassium 2-methylpentanoate; and alkaline earth metal salts of 2-methylpentanoic acid such as calcium 2-methylpentanoate, magnesium 2-methylpentanoate, and barium 2-methylpentanoate.

Next in the liberation step, an acid is added to the aqueous phase containing the salt of 2-methylpentanoic acid (7) to make the phase acidic so as to have the 2-methylpentanoic acid (4) liberated; and the liberated 2-methylpentanoic acid (4) is recovered by separating the 2-methylpentanoic acid (4) from the aqueous phase.

Examples of the acid to be used in the liberation step include organic acids such as formic acid, acetic acid, trifluoroacetic acid, dichloroacetic acid, oxalic acid, tartaric acid, citric acid, p-toluenesulfonic acid, benzenesulfonic acid, and methanesulfonic acid; and inorganic acids such as hydrochloric acid, hydrobromic acid, hydroiodic acid, sulfuric acid, nitric acid, phosphoric acid, and boric acid. Hydrochloric acid is preferred in view of the economy.

The acid may be used either alone or in combination thereof. The acid may be commercially available one.

When the acid is in a solid form, it may be used as such or dissolved in the solvent and/or water used in the nucleophilic substitution reaction.

An amount of the acid is preferably from 1.0 to 6.0 mol per mol of the 2-methylpentanoic anhydride (1) used in the aforesaid nucleophilic substitution reaction in view of the recovery yield.

A temperature of the liberation reaction is preferably from −20 to 70° C., more preferably from 0 to 40° C., in view of the reactivity.

A reaction time differs, depending on a production scale and/or heat removal ability and is preferably from 0.5 to 20 hours in view of the reactivity.

A pH of the aqueous phase is preferably 1.0 or lower, more preferably from −1.0 to +1.0, in view of the recovery yield of the 2-methylpentanoic acid (4). The pH may be determined, for example, by pH test strip or a pH meter after adjusting the temperature of the liquid object at 25° C.

In the liberation step, a solvent may be added, such as a hydrocarbon solvent such as toluene, xylene, pentane, hexane, or heptane; an ether solvent such as tetrahydrofuran, 4-methyltetrahydropyran, or diethyl ether; or a polar solvent such as methyl acetate, ethyl acetate, or acetonitrile. However, the solvent should be removed later, so that the reaction is conducted preferably without a solvent.

The 2-methylpentanoic acid (4) thus recovered can be repeatedly used as a raw material for the condensation reaction, which is economically advantageous.

B. Preparation of 4-methyl-5-nonanol (5)

A process for preparing 4-methyl-5-nonanol (5) in the following chemical reaction formula will be explained. This preparation process includes a step of forming 4-methyl-5-nonanol (5) by a reduction reaction between the 4-methyl-5-nonanone (3) prepared in the aforesaid step A and a reducing agent.

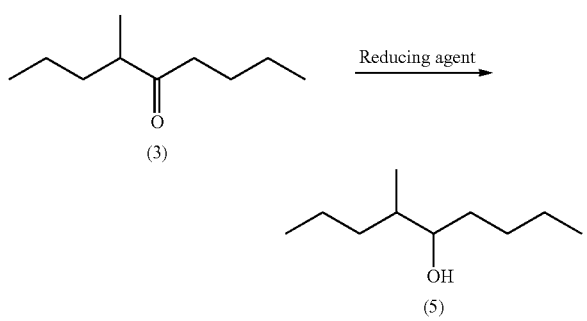

Examples of the reducing agent include alkali metal borohydrides such as lithium borohydride, sodium borohydride, and potassium borohydride; alkaline earth metal borohydrides such as magnesium borohydride and calcium borohydride; alkali metal cyanoborohydrides such as lithium cyanoborohydride, sodium cyanoborohydride, and potassium cyanoborohydride; alkaline earth metal cyanoborohydrides such as magnesium cyanoborohydride and calcium cyanoborohydride; alkali metal tri-sec-butyl borohydrides such as sodium tri-sec-butyl borohydride and lithium tri-sec-butyl borohydride; and diisobutylaluminum hydride, sodium bis(2-methoxyethoxy)aluminum hydride, and lithium aluminum hydride. The alkali metal borohydrides such as sodium borohydride are preferred in view of the economy.

The reducing agent may be used either alone or in combination thereof. The reducing agent may be commercially available one.

An amount of the reducing agent differs, depending on the reducing agent used and is preferably from 0.25 to 5.0 mol per mol of the 4-methyl-5-nonanone (3) in view of the reactivity.

A solvent may be used in the reduction reaction, if necessary. Examples of the solvent include hydrocarbon solvents such as toluene, xylene, and hexane; ether solvents such as tetrahydrofuran, 4-methyltetrahydropyran and diethyl ether; polar solvents such as N,N-dimethylformamide, N,N-dimethylacetamide, N-methylpyrrolidone, acetonitrile, dichloromethane, and chloroform; alcohol solvents such as methanol and ethanol; and water. A proper solvent may be selected, depending on a reducing agent used. For example, an alcohol solvent such as ethanol or a mixed solvent of the alcohol solvent with another solvent is preferred when the alkali metal borohydride is used as the reducing agent.

For example, a mixing ratio in weight in the mixed solvent of the alcohol solvent with water is preferably from 40.0:60.0 to 60.0:40.0 in view of the reactivity.

An amount of the solvent is preferably from 40 to 1000 g per mol of the 4-methyl-5-nonanone, (3) in view of the reactivity.

The solvent may be used either alone or in combination thereof. The solvent may be commercially available one.

A base may be used in the reduction reaction, if necessary. Examples of the base include alkali metal hydroxides such as lithium hydroxide, sodium hydroxide, and potassium hydroxide; alkaline earth metal hydroxides such as calcium hydroxide, magnesium hydroxide, and barium hydroxide; alkali metal carbonates such as sodium carbonate and potassium carbonate; alkaline earth metal carbonates such as calcium carbonate, magnesium carbonate, and barium carbonate; alkali metal hydrogen carbonates such as sodium hydrogen carbonate and potassium hydrogen carbonate; and alkaline earth metal hydrogen carbonates such as calcium hydrogen carbonate and magnesium hydrogen carbonate. The alkali metal hydroxides such as sodium hydroxide are preferred in view of the handling.

The base may be used either alone or in combination thereof. The base may be commercially available one.

When the base is in a solid form, it may be added as such to the reaction mixture or may be dissolved in advance in a solvent to be used in the reduction reaction.

An amount of the base is preferably from 0.00 to 10.00 mol, more preferably from 0.01 to 8.00 mol, per mol of the 4-methyl-5-nonanone (3) in view of the reactivity.

A temperature of the reduction reaction is preferably from −20 to 100° C., more preferably from 10 to 60° C., in view of the reactivity.

A reaction time differs, depending on a solvent used and/or a production scale and is preferably from 2 to 35 hours in view of the reactivity.

Examples of the 4-methyl-5-nonanol (5) include (4R,5R)-4-methyl-5-nonanol of the following formula (5-1), (4S,5S)-4-methyl-5-nonanol of the following formula (5-2), (4R,5S)-4-methyl-5-nonanol of the following formula (5-3), and (4S,5R)-4-methyl-5-nonanol of the following formula (5-4), and a racemate, diastereomeric mixtures, and scalemic mixtures thereof.

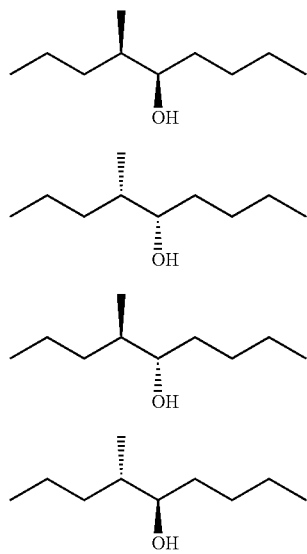

The compounds of the aforesaid formulas (5-1) and (5-2), and the compounds of the aforesaid formulas (5.3) and (5-4) may hereinafter be called "syn-form" and "anti-form", respectively.

The syn-form can be prepared selectively using an alkali metal tri-sec-butyl borohydride, and the anti-form can be prepared selectively using lithium aluminum hydride.

EXAMPLES

The present invention will be further described with reference to the following Examples. It should be construed that the invention is not limited to or by the Examples.

The term "purity" as used herein means an area percentage obtained by gas chromatography (GC) analysis, unless otherwise described. The term "production ratio" means a relative ratio in area percentages determined by GC analysis. The "yield" is calculated from area percentages obtained by GC analysis.

In each of Examples, monitoring of the reactions and calculation of the yield were carried out under the following GC conditions I.

<GC conditions I>: GC: Capillary gas chromatograph GC-2014, ex Shimadzu Corporation; column: DB-5, 0.25 mm×0.25 mmϕ×30 m; carrier gas: He (1.55 mL/min), detector: FID; column temperature: 70° C., elevated by 5° C./min, to 230° C.

A syn-form:anti-form ratio of the 4-methyl-5 nonanol (5) was analyzed under the following GC conditions II.

<GC conditions>: CC: Capillary gas chromatograph GC-2014, ex Shimadzu Corporation; column: CYCLO-DEX-B, 0.25 mm×0.25 mmϕ×30 m; carrier gas: He (1.55 mL/min), detector; FID; column temperature: 70° C., elevated by 5° C./min, to 230° C.

The yield was calculated by the following equation in consideration of purities (% GC) of a raw material and a product.

Yield (%)={[(weight of a product obtained by reaction×% GC)/molecular weight of a product]÷[(weight of a starting material in reaction×% GC)/molecular weight of a starting material]}100

Example 1

Preparation of 2-methylpentanoic anhydride (1)

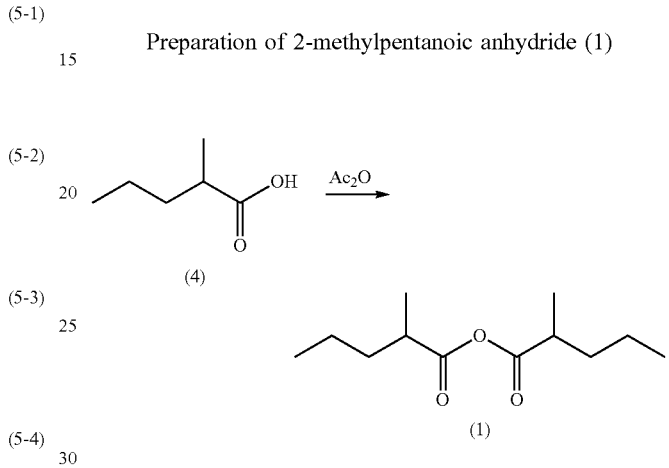

First, a distillation tower was corrected to one of the ports of a reactor and a fractionating tower was connected to the outlet of the, distillation tower. Further, a thermometer and a condenser were connected to the fractionating tower.

The 2-methylpentanoic acid (4) (459.41 g, 3.955 mol) and acetic anhydride ($Ac_2O$) (817.33 g, 7.91 viol) were added to the aforesaid reactor at room temperature. The fractionating tower was then closed and the mixture was stirred at an internal temperature of 160° C. and normal pressure for 30 minutes. Next, the fractionating tower was opened and acetic acid was subjected to distillation at an internal temperature of 160° C. and normal pressure, until an acetic acid content in the distillate containing at least 2.0 acetic acid, acetic anhydride, and acetic 2-methylpentanoic anhydride became 5.0%. Further, the pressure was reduced gradually to 64 mmHg at an internal temperature of 160° C. to distill acetic anhydride off. After the acetic anhydride content in the distillate containing at least acetic anhydride, 2-methylpentanol, acetic 2-methylpentanoic anhydride, and 2-methylpentanoic anhydride became 0.5%, the pressure was reduced to 3 mmHg to distill 2-methylpentanoic anhydride (1) off. The internal temperature decreased to 140° C. at that time. The 2-methylpentanoic anhydride (1) (402.88 g, 1.88 mol) was obtained in a yield of 95.2%.

The following is the spectrum data of the 2-methylpentanoic anhydride (1) thus obtained.

[Nuclear magnetic resonance spectrum] $^1$H-NMR (500 MHz, $CDCl_3$): δ=0.92(6H, t, J=7.3 Hz), 1.20(6H, d, J=7.3 Hz), 1.32-1.49(4H, m, 1.40-1.74(4H, m), 2.54(2H, tq, J=7.0, 7.0 Hz); $^{13}$C-NMR (500 MHz, $CDCl_3$): δ=13.85, 16.22, 20.11, 35.18, 40.26, 172.48

[Mass spectrum] EI-Mass spectrum (70 eV): m/z 172($M^+$-42), 143, 99, 71, 55, 43, 29

[Infrared absorption spectrum] (NaCl): v=2961, 2937, 2876, 1813, 1746, 1460, 1038, 1018, 991

Example 2A

Preparation of 4-methyl-5-nonanone (3)

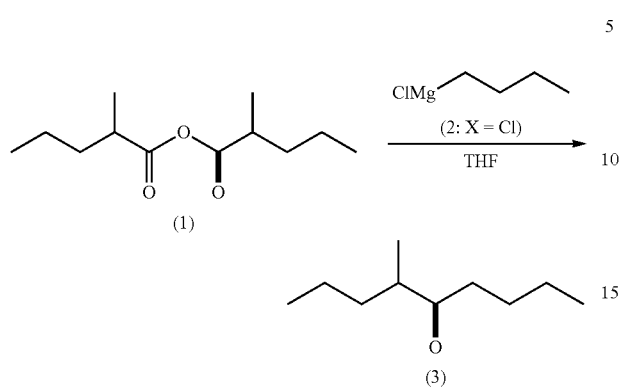

Magnesium (54.42 g, 2.27 gram atoms) and tetrahydrofuran (THF) (639.90 g) were added to a reactor at room temperature and stirred at from 60 to 65° C. for 30 minutes. After the stirring, 1-chlorobutane (197.17 g, 2.13 mol) was added dropwise to the reactor at from 60 to 75° C. and the reaction mixture was stirred at from 75 to 80° C. for 2 hours to prepare butylmagnesium chloride (2: M=Cl).

Then, tetrahydrofuran (792.26 g) and 2-methylpentanoic anhydride (1) (456.46 g, 2.13 mol) were added to another reactor and the whole amount of the butylmagnesium chloride (2: M=Cl) obtained above was added dropwise at from −5 to 10° C. After the completion of the dropwise addition, the reaction mixture was stirred at from 0 to 10° C. for 3 hours, Then, acetic acid (168.05 g) and water (826.68 g) were added to the reaction mixture in the reactor to cause phase separation and the aqueous phase thus obtained was removed. An aqueous 25 wt % sodium hydroxide solution (469.26 g, 2.93 mol of sodium hydroxide) and water (1279.80 g) were added to the organic phase in the reactor at room temperature and stirred for 17 minutes for neutralization. An organic phase and an aqueous phase (2604.29 g) containing sodium 2-methylpentanoate (7: Y=Na) Were obtained by phase separation. Subsequently, it was confirmed using a pH test strip that the aqueous phase containing sodium 2-methyl pentanoate (7: Y=Na) had a pH of 14.0. Next, acetic acid (6,09 g) and water (304.71 g) were added to the resulting organic phase to wash the same, followed by phase separation. The organic phase was concentrated at a reduced pressure and the residue was subjected to distillation at a reduced pressure to obtain 4-methyl-5-nonanone (3) (307.24 g, 1.96 mol, purity: 99.69%) in a yield of 92.0%.

The following is spectrum data of the 4-methyl-5-nonanone (3) thus prepared.

[Nuclear magnetic resonance spectrum] $^1$H-NMR (500 MHz, CDCl$_3$): δ=0.87(3H, t, J=7.3 Hz), 0.89(3H, t, J=7.3 Hz), 1.04(3H, d, J=6.9 Hz), 1.14-1.66(2H, m), 1.24-1.33 (4H, m), 1.53(2H, tt, J 7.6, 7.6 Hz), 2.41(2H, dt, 2.7, 7.5 Hz), 2.51(1H, tq, J=6.8, 6.8 Hz); $^{13}$C-NMR (500 MHz, CDCl$_3$): δ=13.87, 14.09, 16.30, 20.46, 22.39, 25.78, 35.16, 40.82, 46.06, 215.11

[Mass spectrum] EI-Mass spectrum (70 eV): m/z 156; (M$^+$), 141, 127, 99, 85, 71, 57, 43, 29

[Infrared absorption spectrum] (NaCl): ν=2960, 2933, 2874, 1713, 1459, 1378

Example 2B

Recovery of 2-methyl-1-pentanoic Acid (4)

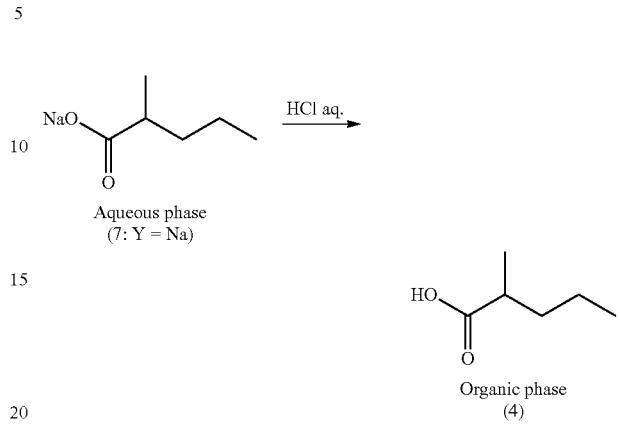

The aqueous phase (2604.29 g) containing sodium 2-methylpentanoate (7: Y=Na) obtained in Example 2A was added to a reactor and an aqueous 20 wt % hydrochloric acid (570.93 g, 3.13 mol of hydrogen chloride) was added dropwise at from 10 to 20° C. After the completion of the dropwise addition, the reaction mixture was stirred at from 15 to 25° C. for one hour. The reaction mixture was left to stand. After 2-methyl-1-pentanoic acid (4) was liberated and the reaction mixture separated into an organic phase and an aqueous phase, the aqueous phase was removed by a phase separation to take up the Organic phase containing the 2-methyl-1-pentatonic acid (4). It was confirmed by a 071 test strip that the aqueous phase had a pH of 1.0. The organic phase thus obtained was concentrated at a reduced. pressure to obtain 2-methyl-1-pentanoic acid (4) (179.19 g, 2.03 mol) in a yield of 95.3%.

The following is spectrum data of the 2-methyl-1-pentanoic acid (4) thus recovered.

[Nuclear magnetic resonance spectrum] $^1$H-NMR (500 MHz, CDCl$_3$): δ=0.91(3H, t, J=7.3 Hz), 1.17(3H, d, J=7.3 Hz), 1.37(2H, tt, J=7.1, 7.1 Hz), 1.36-1.72(1H, m), 2.47 (1H, tq, J=6.9, 6.9 Hz), 11.66(1H, br. s); $^{13}$C-NMR (500 MHz, CDCl$_3$): δ=13.89, 16,77, 20.30, 35.64, 39.17, 183.77

[Mass spectrum] EI-Mass spectrum (70 eV): m/z 115 (M$^+$-1), 101, 87, 74, 43

[Infrared absorption spectrum] (NaCl): ν=2962, 2937, 2876, 2662, 1707, 1467, 1417, 1246, 1218, 935

Example 3

Preparation of 2-methylpentanoic anhydride (1), using the recovered 2-methylpentanoic acid (4)

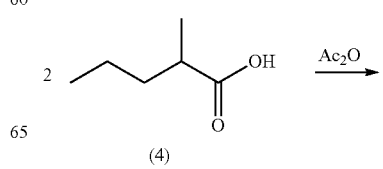

-continued

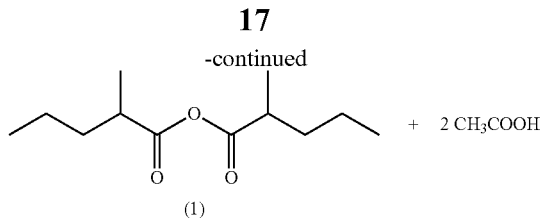

First, a distillation tower was connected to one of the ports of a reactor and a fractionating tower was connected to the outlet of the distillation tower. Further, a thermometer and a condenser were connected to the fractionating tower.

The 2-methylpentanoic acid (4) (179.19 g, 2.03 mol) recovered in Example 2B and acetic anhydride (Ac$_2$O) (414.49 g, 4.06 mol) were added to the aforesaid reactor at room temperature. The fractionating tower was then closed and the mixture was stirred at an internal temperature of 160° C. and normal pressure for 30 minutes. Next, the fractionating tower was opened and acetic acid was subjected to distillation at an internal temperature of 160° C. and normal pressure, until an acetic acid content in the distillate containing at least acetic acid, acetic anhydride, and acetic 2-methylpentanoic anhydride became 5.0%. Further, the pressure was reduced gradually to 64 mmHg at an internal temperature of 160° C. to distill acetic anhydride off. After the acetic anhydride content in the distillate containing at least acetic anhydride, 2-methylpentanol, acetic 2-methylpentanoic anhydride, and 2-methylpentanoic anhydride became 0.5%, the pressure was reduced to 3 mmHg to distill 2-methylpentanoic anhydride (1) off. The internal temperature decreased to 140° C. at that time. The 2-methylpentanoic anhydride (1) (366.45 g, 1.71 mol) was obtained in a yield of 84.4%.

The spectrum data of 2-methylpentanoic anhydride (1) obtained above were the sari e as those of the 2-methylpentanoic anhydride (1) obtained in Example 1

Example 4

Preparation of 4-methyl-5-nonanol (5)

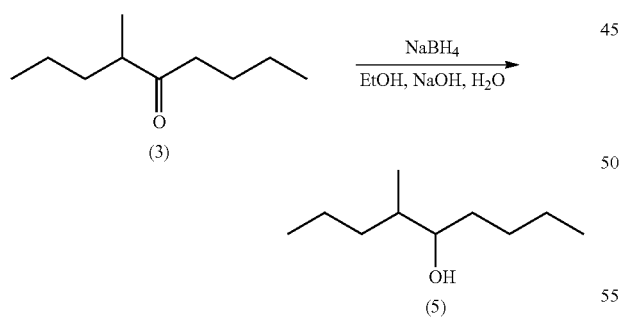

Sodium borohydride (NaBH$_4$) (11.77 g, 0.31 mol), ethanol (97.88 g), an aqueous 25 wt % sodium hydroxide solution (2.92 g, 0.018 mol of sodium hydroxide), and water (78.77 g) were added to a reactor at room temperature and 4-methyl-5-nonanone (3) (140.00 g, purity: 99.69%, 0.89 mol) was added dropwise at from 15 to 25° C. After the completion of the dropwise addition, the reaction mixture was stirred at from 30 to 35° C. for 10 hours and then phase-separated to obtain an organic phase. Acetic acid (10 g) and water (100 g) were added to the resulting organic phase to cause phase separation again. Subsequently, the organic phase was concentrated at a reduced pressure and the residue was subjected to distillation at a reduced pressure to obtain 4-methyl-5-nonanol (5) (138.14 g, 0.82 mol, purity: 99.75%, (syn-form):(anti-form)=50:50) in a yield of 97.5%.

The following is the spectrum data of the 4-methyl-5-nonanol (5) thus obtained.

[Nuclear magnetic resonance spectrum] $^1$H-NMR (500 MHz, CDCl$_3$): δ=0.86(3H, t, J=6.9 Hz), 0.89(3H, t, J=6.9 Hz), 0.90(3H, t, J=7.1), 1.04-1.56(12H, m), 3.40-3.50(1H, m); $^{13}$C-NMR (500 MHz, CDCl$_3$). J =13.48, 14.07, 14.30, 14.34, 15.18, 20.39, 20.44, 22.77, 22.79, 28.32, 28.45, 33.01, 34.10, 34.13, 35.58, 37.86, 38.52, 75.15, 76.02

[Mass spectrum] EI-Mass spectrum (70 eV): m/z 157 (M$^+$−1), 140, 101, 87, 69, 55, 41

[infrared absorption spectrum] (NaCl): ν=3363, 2.958, 2931, 2873, 1467, 1379, 1012, 976

The invention claimed is:

1. A process for preparing 4-methyl-5-nonanone of the following formula (3):

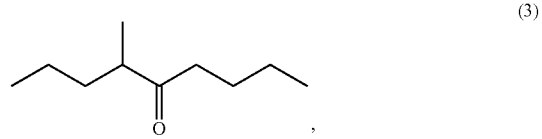

the process comprising at least a step of
subjecting 2-methylpentanoic anhydride of the following formula (1):

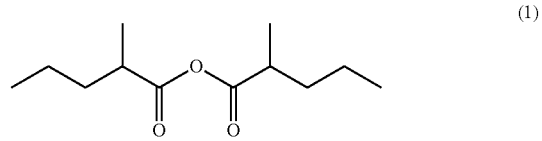

and an n-butyl nucleophilic reagent of the following general formula (2):

MCH$_2$CH$_2$CH$_2$CH$_3$ (2)

in which M represents Li, MgZ$^1$, or ZnZ$^1$, wherein Z$^1$ represents a halogen atom or an n-butyl group,
to a nucleophilic substitution reaction to produce 4-methyl-5-nonanone (3).

2. The process according to claim 1, further comprising subjecting 2-methylpentanoic acid of the following formula (4):

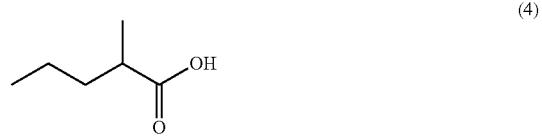

to a condensation reaction to produce the aforesaid 2-methylpentanoic anhydride (1).

3. The process according to claim 1, further comprising during or after the aforesaid nucleophilic substitution reaction, recovering 2-methylpentanoic acid which was by-produced in the nucleophilic substitution reaction.

4. The process according to claim 3, further comprising subjecting the recovered 2-methylpentanoic acid to a condensation reaction to produce 2-methylpentanoic anhydride (1).

5. The process according to claim 4, wherein the obtained 2-methylpentanoic anhydride (1) is used in the nucleophilic substitution reaction.

6. The process according to claim 4, further comprising repeating the nucleophilic substitution reaction with use of the obtained 2-methylpentanoic anhydride (1) as a raw material for the nucleophilic substitution reaction.

7. A process for preparing 4-methyl-5-nonanol of the following formula (5):

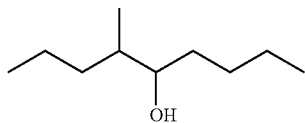
(5)

the process comprising at least steps of
preparing 4-methyl-5-nonanone (3) according to any one of claims 1-6; and
subjecting the obtained 4-methyl-5-nonanone (3) and a reducing agent to a reduction reaction to produce 4-methyl-5-nonanol (5).

8. The process according to claim 2, further comprising during or after the aforesaid nucleophilic substitution reaction, recovering 2-methylpentanoic acid which was by-produced in the nucleophilic substitution reaction.

9. The process according to claim 8, further comprising subjecting the recovered 2-methylpentanoic acid to a condensation reaction to produce 2-methylpentanoic anhydride (1).

10. The process according to claim 9, wherein the obtained 2-methylpentanoic anhydride (1) is used in the nucleophilic substitution reaction.

11. The process according to claim 9, further comprising repeating the nucleophilic substitution reaction with use of the obtained 2-methylpentanoic anhydride (1) as a raw material for the nucleophilic substitution reaction.

* * * * *

UNITED STATES PATENT AND TRADEMARK OFFICE
CERTIFICATE OF CORRECTION

PATENT NO. : 10,882,805 B2
APPLICATION NO. : 16/722123
DATED : January 5, 2021
INVENTOR(S) : Miyake et al.

Page 1 of 1

It is certified that error appears in the above-identified patent and that said Letters Patent is hereby corrected as shown below:

On the Title Page

(57) Abstract, Line 8: Please correct "substitution. reaction Coproduce" to read -- substitution reaction to produce --

In the Specification

Column 7, Line 64: Please correct "(13)" to read -- (3) --

Column 13, Line 65: Please correct "CC:" to read -- GC: --

Column 14, Line 37: Please correct "7.91 viol" to read -- 7.91 mol --

Column 16, Line 34: Please correct "071" to read -- pH --

Signed and Sealed this
Seventeenth Day of August, 2021

Drew Hirshfeld
*Performing the Functions and Duties of the*
*Under Secretary of Commerce for Intellectual Property and*
*Director of the United States Patent and Trademark Office*